(12) United States Patent
Wessely et al.

(10) Patent No.: US 12,018,286 B2
(45) Date of Patent: Jun. 25, 2024

(54) GENERATING HUMAN PODOCYTE CELLS

(71) Applicant: The Cleveland Clinic Foundation, Cleveland, OH (US)

(72) Inventors: Oliver Wessely, Cleveland Heights, OH (US); Uyen Wessely, Cleveland Heights, OH (US); Jan Jensen, Shaker Heights, OH (US); Michael Bukys, Cleveland, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 637 days.

(21) Appl. No.: 17/012,651

(22) Filed: Sep. 4, 2020

(65) Prior Publication Data

US 2021/0079357 A1    Mar. 18, 2021

Related U.S. Application Data

(60) Provisional application No. 62/899,582, filed on Sep. 12, 2019.

(51) Int. Cl.
  *C12N 5/071*    (2010.01)
(52) U.S. Cl.
  CPC ........ *C12N 5/0684* (2013.01); *C12N 2500/90* (2013.01); *C12N 2501/155* (2013.01); *C12N 2501/415* (2013.01); *C12N 2501/42* (2013.01); *C12N 2501/999* (2013.01); *C12N 2506/25* (2013.01)
(58) Field of Classification Search
  CPC .................................................. C12N 5/0684
  See application file for complete search history.

(56) References Cited

FOREIGN PATENT DOCUMENTS

| CN | 105087467 | 11/2015 |
|---|---|---|
| EP | 3027737 | 12/2018 |

OTHER PUBLICATIONS

Qian et al. (2019, Scientific Reports, vol. 9:2765, pp. 1-12) (Year: 2019).*
Ueda et al. (2008, J. Am. Soc. Nephrol., vol. 19(4), pp. 685-694) (Year: 2008).*
Krtil et al., Culture methods of glomerular podocytes. Kidney Blood Press Res. 2007;30(3):162-74.
Marinho et al., Systematic optimization of human pluripotent stem cells media using Design of Experiments. Sci Rep. May 5, 2015;5:9834.
Morizane et al., Nephron organoids derived from human pluripotent stem cells model kidney development and injury. Nat Biotechnol. Nov. 2015;33(11):1193-200.
Musah et al., Mature induced-pluripotent-stem-cell-derived human podocytes reconstitute kidney glomerular-capillary-wall function on a chip. Nat Biomed Eng. 2017;1:0069.
Rauch et al., Differentiation of human iPSCs into functional podocytes. PLoS One. Sep. 17, 2018;13(9):e0203869.
Ronconi et al., Regeneration of glomerular podocytes by human renal progenitors. J Am Soc Nephrol. Feb. 2009;20(2):322-32.
Song et al., The directed differentiation of human iPS cells into kidney podocytes. PLoS One. 2012;7(9):e46453.

* cited by examiner

*Primary Examiner* — Anoop K Singh
*Assistant Examiner* — David A Montanari
(74) *Attorney, Agent, or Firm* — Jason R. Bond; Casimir Jones, S.C.

(57) ABSTRACT

Provided herein are compositions, systems, kits, and methods for generating human podocyte cells by contacting human nephron progenitor cells with an FGFR pathway inhibitor, a BMP pathway inhibitor, and a WNT pathway inhibitor. In certain embodiments, the nephron progenitor cells are further contacted with at least one factor selected from: BMP4, BMP7, lysophosphatidic acid, and gamma-secretase inhibitor XX. In certain embodiments, the contacting the nephron progenitor cells is performed under serum-free conditions.

12 Claims, 11 Drawing Sheets

Podocyte Differentiation

GENERATING HUMAN PODOCYTE CELLS

The present application claims priority to U.S. Provisional application Ser. No. 62/899,582, filed Sep. 12, 2019, which is herein incorporated by reference in its entirety.

STATEMENT REGARDING FEDERAL FUNDING

This invention was made with government support under DK107357 awarded by National Institutes of Health. The government has certain rights to the invention.

FIELD

Provided herein are compositions, systems, kits, and methods for generating human podocyte cells by contacting human nephron progenitor cells with an FGFR pathway inhibitor, a BMP pathway inhibitor, and a WNT pathway inhibitor. In certain embodiments, the nephron progenitor cells are further contacted with at least one factor selected from: BMP4, BMP7, lysophosphatidic acid, and gamma-secretase inhibitor XX. In certain embodiments, the contacting the nephron progenitor cells is performed under serum-free conditions.

BACKGROUND

Podocytes are an important cell type within the kidney. They provide the interface between the vasculature and the renal tubule. Podocyte loss/malfunction causes acute or chronic kidney injury. Moreover, podocyte injury is often caused by non-kidney diseases such as lupus or HIV and as a response to invasive therapies such as radiation or chemotherapy. In the absence of therapeutic interventions that augment podocytes, the standard of care is normally dialysis. Moreover, due to their exposed position towards the blood stream, drugs and other therapeutic agents often impact podocyte health/functionality. Thus, assessing any effect on podocytes is an important aspect in drug development.

The availability of large numbers of normal terminally differentiated human podocytes is a major impediment in the field. While there are protocols available that can isolate primary podocytes from kidneys, these podocytes cannot be expanded to significant numbers and are therefore not a viable source for any application requiring large numbers of cells. Other sources are podocyte cell lines, yet they often show poor differentiation potential, are transformed by the introduction of oncogenes or are of non-human origin.

SUMMARY

Provided herein are compositions, systems, kits, and methods for generating human podocyte cells by contacting human nephron progenitor cells with an FGFR pathway inhibitor, a BMP pathway inhibitor, and a WNT pathway inhibitor. In certain embodiments, the nephron progenitor cells are further contacted with at least one factor selected from: BMP4, BMP7, lysophosphatidic acid, and gamma-secretase inhibitor XX. In certain embodiments, the contacting the nephron progenitor cells is performed under serum-free conditions.

In some embodiments, provide herein are methods of generating podocyte cells (e.g., human podocyte cells) comprising: a) contacting a population of nephron progenitor cells (e.g., human nephron progenitor cells) with an FGFR pathway inhibitor, a BMP pathway inhibitor, and a WNT pathway inhibitor; and b) culturing at least a portion of the population of nephron progenitor cells such that a population of podocyte cells is generated. In other embodiments, the nephron progenitor cells are not exposed to serum during the culturing or during the contacting.

In certain embodiments, the methods further comprise, prior to step b), contacting the nephron progenitor cells with BMP4. In other embodiments, the methods further comprise, prior to step b), contacting the nephron progenitor cells with BMP7. In other embodiments, the methods further comprise, prior to step b), contacting the nephron progenitor cells with lysophosphatidic acid (LPA). In other embodiments, the methods further comprise, prior to step b), contacting the nephron progenitor cells with a Notch pathway inhibitor. In particular embodiments, the Notch pathway inhibitor comprises gamma-secretase inhibitor XX. In particular embodiments, the culturing is conducted for 1-2 days, 1-5 days, or 2-4 days. In some embodiments, the nephron progenitor cells are not exposed to a transforming growth factor beta (TGFβ) pathway agonist during the culturing or during the contacting.

In certain embodiments, the methods further comprise, prior to step a), contacting a population of posterior intermediate mesoderm cells with a GSK-3 inhibitor (e.g., CHIR) and culturing at least a portion of the population of posterior intermediate mesoderm cells such that the population of nephron progenitor cells is generated. In some embodiments, the methods further comprise contacting a population of late primitive streak cells with Activin and culturing at least a portion of the population of late primitive streak cells such that the population posterior intermediate mesoderm cells is generated. In further embodiments, the methods further comprise contacting a population of pluripotent stem cells with a GSK-3 inhibitor and culturing at least a portion of the population of pluripotent stem cells such that the population late primitive streak cells is generated.

In certain embodiments, provided here are compositions comprising: a cell, wherein the cell comprises: an exogenous FGFR pathway inhibitor, an exogenous BMP pathway inhibitor, and an exogenous WNT pathway inhibitor, and wherein the cell is a nephron progenitor cell or a podocyte cell.

In some embodiments, provided herein are compositions comprising: cell culture media, wherein the cell culture media comprises: i) an FGFR pathway inhibitor, a BMP pathway inhibitor, and a WNT pathway inhibitor; and ii) a nephron progenitor cell or a podocyte cell. In certain embodiments, the culture media is serum-free. In other embodiments, the cell or media is free of an exogenous transforming growth factor beta (TGFβ) pathway agonist. In further embodiments, the cell or media further comprises at least one factor selected from: exogenous BMP4, exogenous BMP7, exogenous lysophosphatidic acid, and exogenous gamma-secretase inhibitor XX.

In certain embodiments, the cells are nephron progenitor cells, and wherein the FGFR pathway inhibitor, the BMP pathway inhibitor, and the WNT pathway inhibitor are present in the culture media at concentrations that would cause at least a portion of the nephron progenitor cells to become podocyte cells when cultured in the media for at least 1 day or at least 2 days.

In some embodiments, provided here are kits and systems comprising, or consisting essentially of, or consisting of: a) a population of nephron progenitor cells (or a population of induced pluripotent stem cells) present in a cell culture container; and b) an FGFR pathway inhibitor present in a first container; c) a BMP pathway inhibitor present in the first container or a second container, and d) a WNT pathway inhibitor present in the first or second container, or present in a third container. In certain embodiments, the kits and systems further comprise culture media inside the culture container, and wherein the culture media is serum-free.

In certain embodiments, provided herein are methods of implanting at least a portion of the podocyte cells, generated from any of the methods described herein, into the kidney of a patient (e.g., a patient with kidney failure). In other embodiments, provided here are methods comprising contacting a candidate drug with a least a portion of the podocyte cells, generated from any of the methods described herein, and measuring the response of the podocytes (e.g., to determine if the candidate drug is toxic or not to the podocyte cells).

In some embodiments, the podocytes express the following genes: WT1, MAFB, FOXC2, FOXD1, LMX1B, TCF21, NPHS1, NPHS2 and PODXL. In further embodiments, the FGFR pathway inhibitor comprises BGJ398. In other embodiments, the BMP pathway inhibitor comprise LDN193189. In other embodiments, the WNT pathway inhibitor comprises IWP2. In certain embodiments, the Notch pathway inhibitor is selected from the group consisting of: DAPT, MRK-003, MRK-0752, z-Ile-leu-CHO, gamma secretase inhibitor, L-685,485, LY411575, Compound E, F-03084014, RO4929097, BMS-906024, Dapt, FLI-06, YO-01027, LY450139, E2012, TC-E 5006, Avagacestat, Begacestat, BMS299897, Compound E, Compound W, DBZ, Flurizan, JLK6, L-685,458, MRK560, and PF3084014. In particular embodiments, the BMP pathway inhibitor is selected from the group consisting of: DMH1, DMH2, Dorsopmorphin, K02288, LDN214117, ML347, and Noggin. In some embodiments, the FGFR pathway inhibitor is selected from the group consisting of: PD0325901, Arctigenin, PD184352, PD198306, PD334581, SL 327, U0126, a MEK inhibitor, a FGFR inhibitor, a MAPK inhibitor, MEK162, GSK1120212, PD325901, CI-1040, TAK-733, Selumetinib and XL518.

DESCRIPTION OF THE FIGURES

The patent or application file contains at least one drawing executed in color. Copies of this patent or patent application publication with color drawings will be provided by the Office upon request and payment of the necessary fee.

DETAILED DESCRIPTION

Figure 1A:
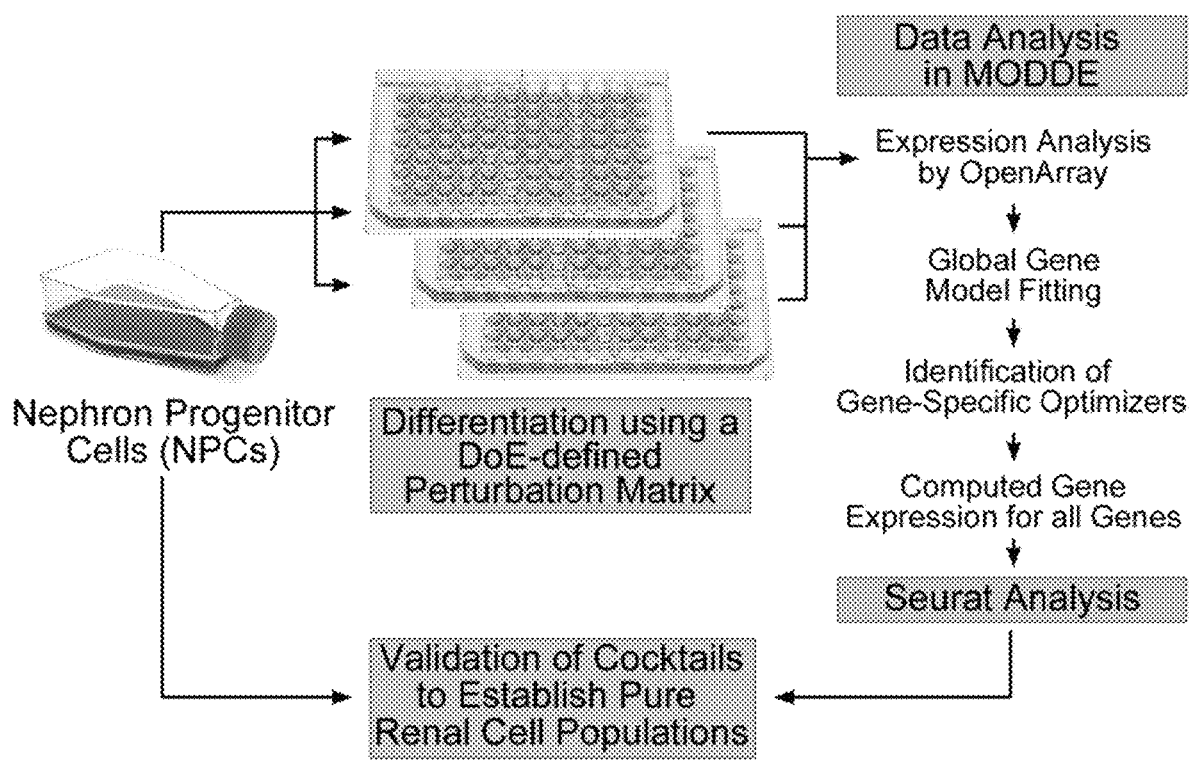
FIG. 1. Analysis of the Multifactorial Space Identifying a Protocol for Podocyte Differentiation. (A) Workflow used to identify conditions to differentiate nephron progenitor cells into podocytes. (B) List of the growth factor signaling agonists and antagonists that were tested in the Design-of-Experiment (DoE) approach (blue box) and the list of genes analyzed using an OpenArray® qPCR panel (green box). (C) UMAP plots from the Seurat analysis of the gene specific optimizers obtained from the OpenArray® qPCR data identifying four distinct clusters representing different cell states. (D) Heatmap demonstrating that each of the clusters is characterized by a distinct gene expression pattern. (E, F) Violin blots of genes characteristic for nephron progenitor cells (SIX2, SALL1, CITED1), renal vesicle cells (PAX8, LHX1, FGF8) and podocytes (MAFB, WT1, FOXD1, NPHS1, NPHS2, PODXL) demonstrating the Cluster 3 represents conditions that differentiate NPCs into podocytes.
Figure 1B:
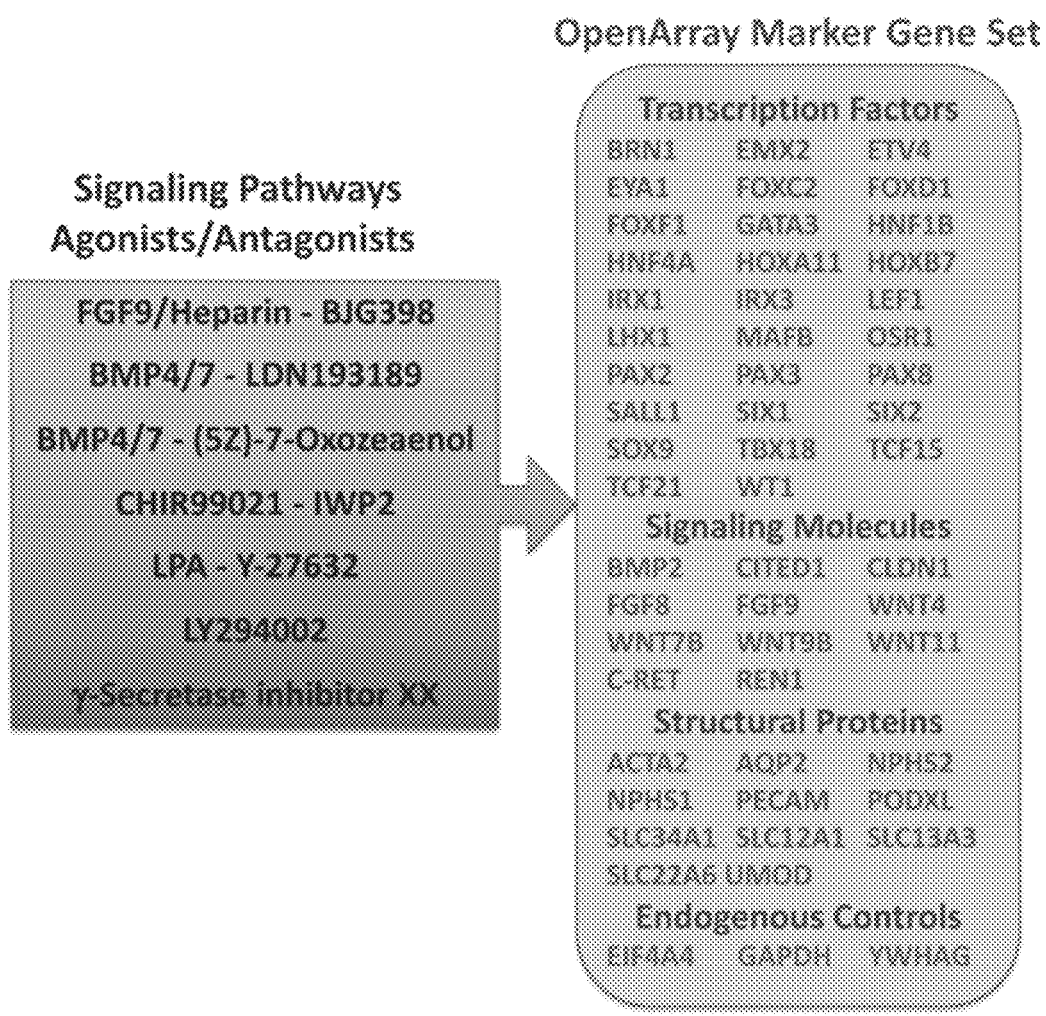
Figure 1C:
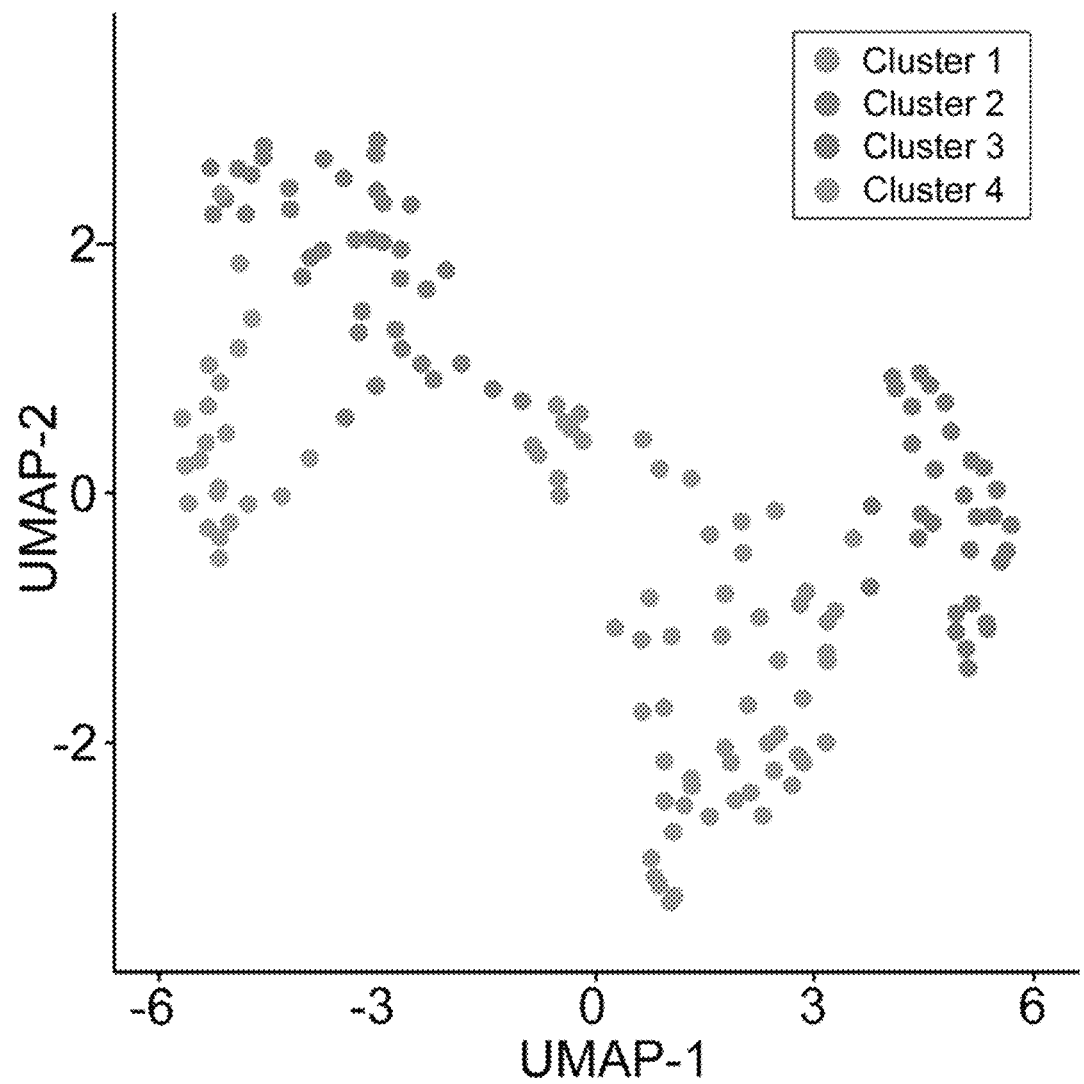
Figure 1D:
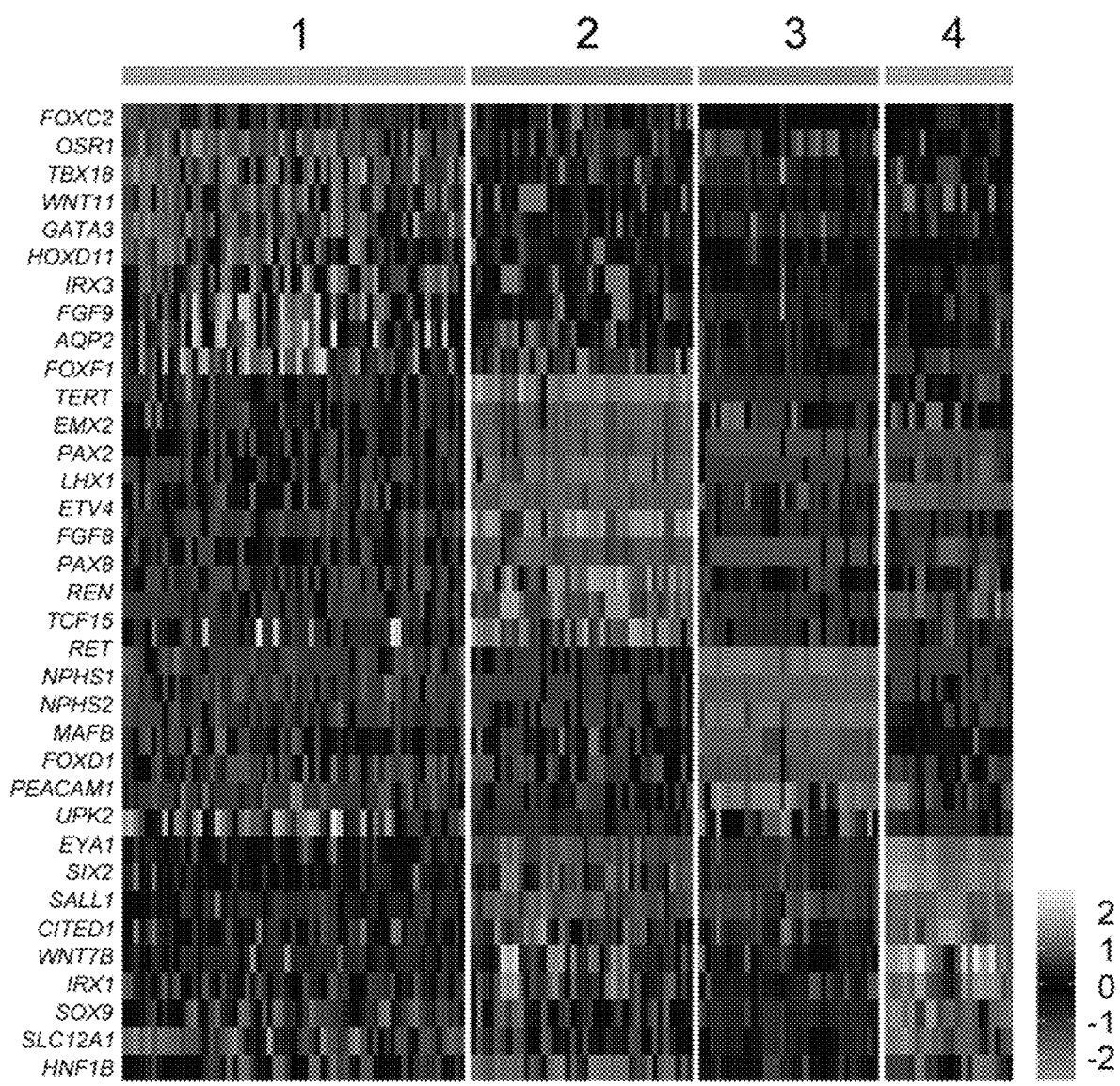
Figure 1E:
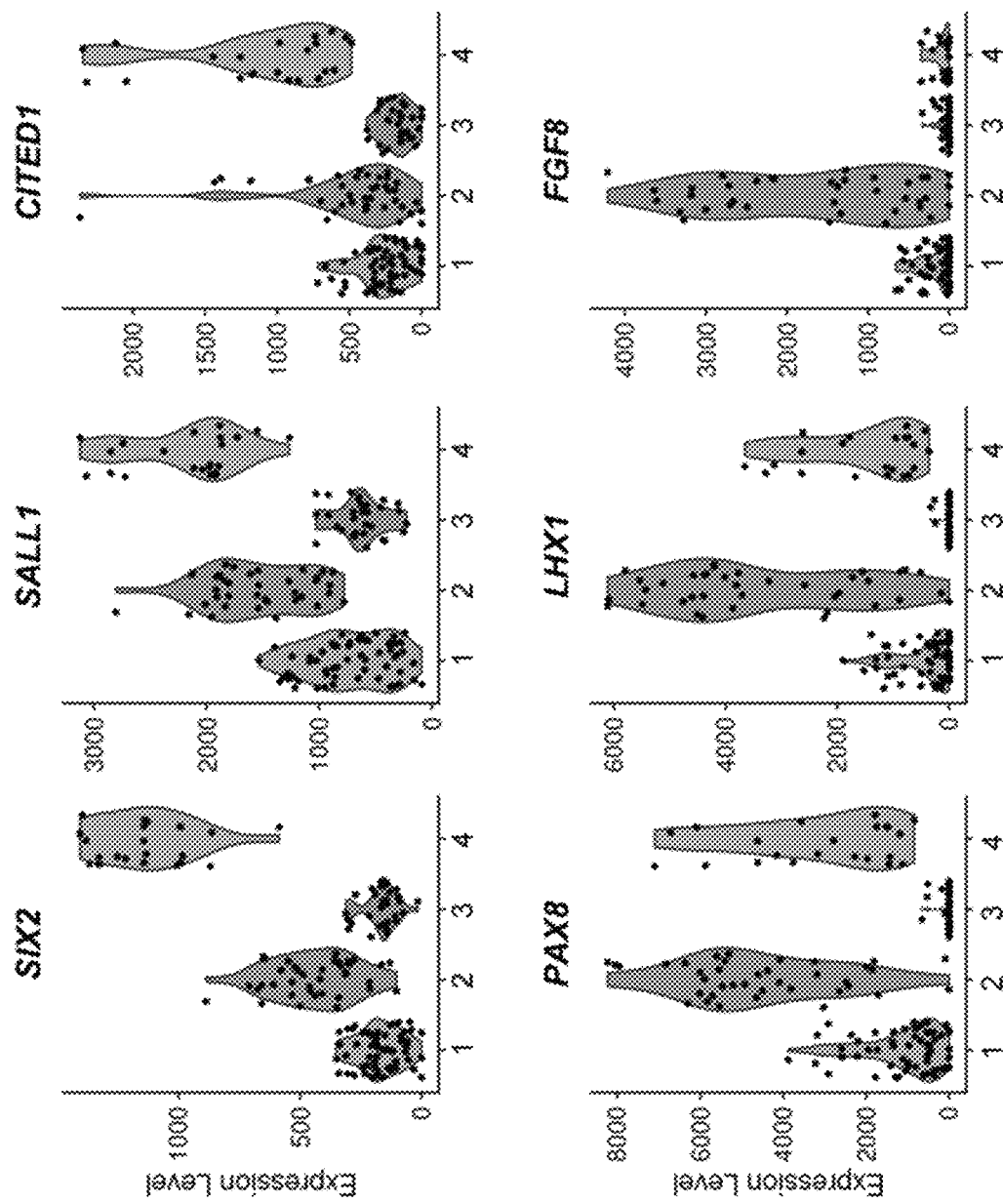
Figure 1F:
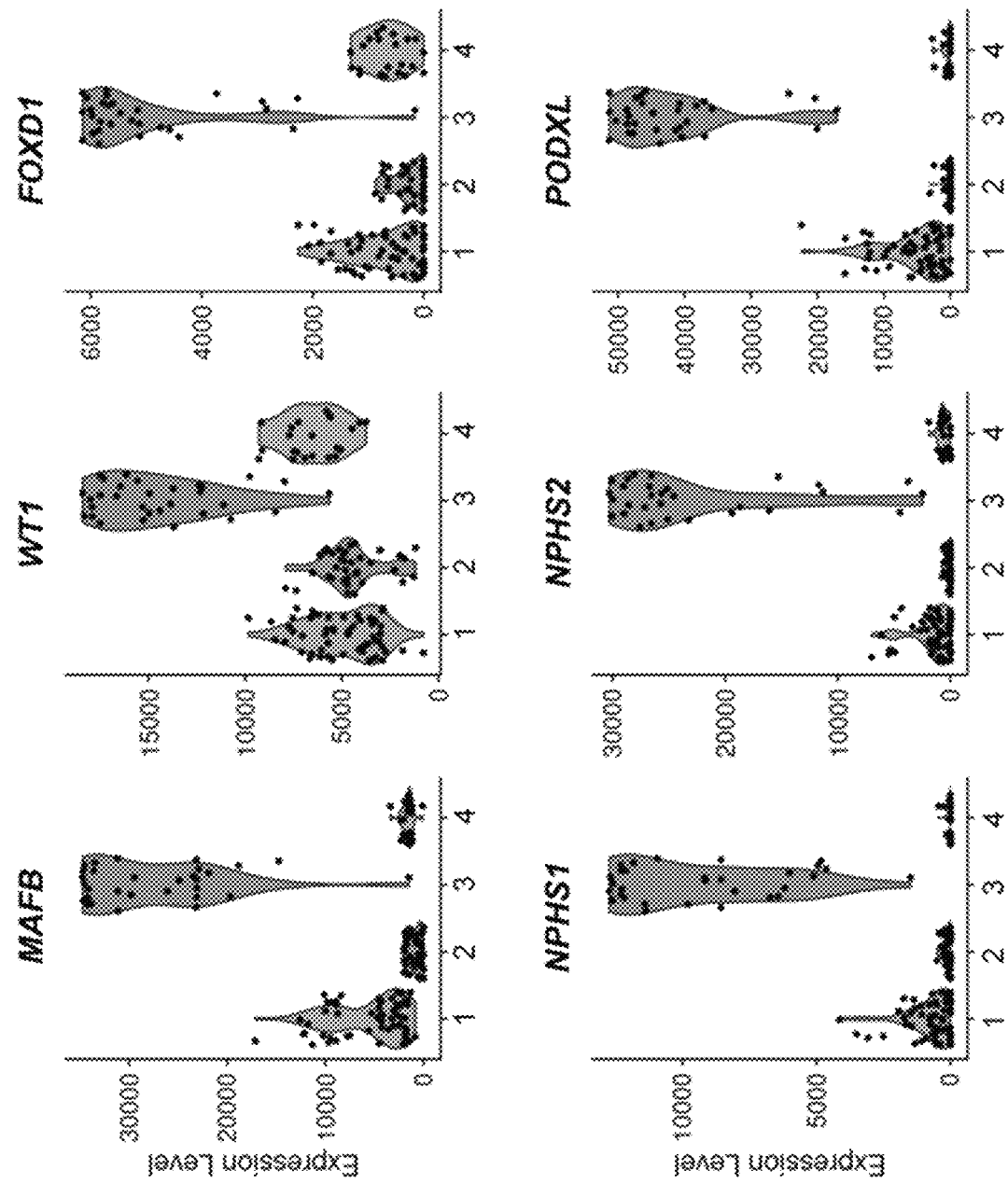
Figure 2:
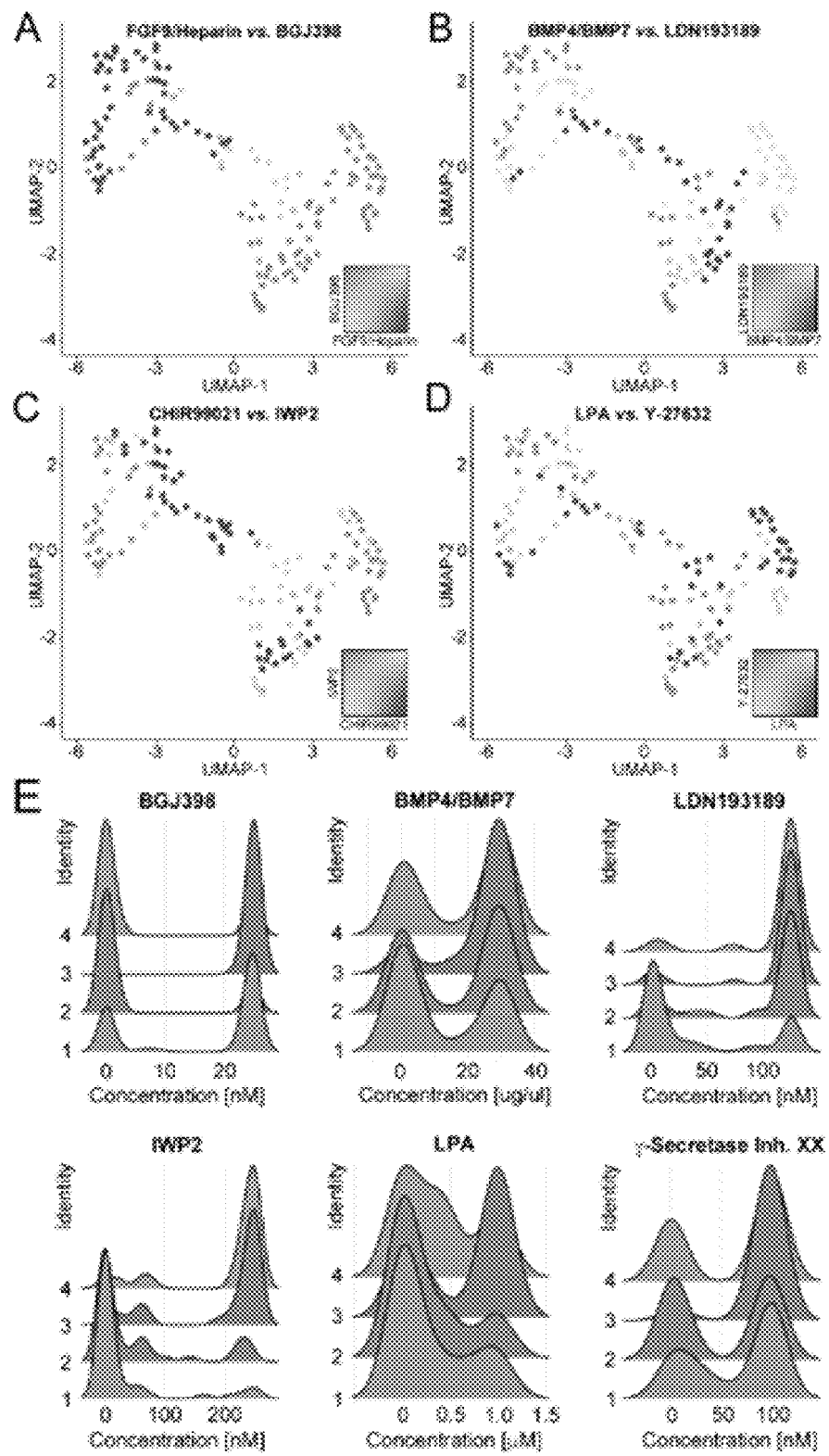
FIG. 2. Identification of the Signaling Agonists/Antagonists Determining Cell Type Specification. (A-D) Overlay of UMAP plots with the amount of signaling agonists and antagonists for FGF (A), BMP (B), WNT (C) and Hippo signaling (D), which were used in the DoE experiments to obtain the specific cell populations. (E) Ridgeplots for individual signaling agonists and/or antagonists demonstrating the concentration required to differentiate cells into the individual cell clusters identified in FIG. 1C. Note that the podocytes (Cluster 3) is determined by a combinatorial input unique from the other cell clusters.

Provided herein are compositions, systems, kits, and methods for generating human podocyte cells by contacting human nephron progenitor cells with an FGFR pathway inhibitor, a BMP pathway inhibitor, and a WNT pathway inhibitor. In certain embodiments, the nephron progenitor cells are further contacted with at least one factor selected from: BMP4, BMP7, lysophosphatidic acid, and gamma-secretase inhibitor XX. In certain embodiments, the contacting the nephron progenitor cells is performed under serum-free conditions.

The podocytes generated with the methods and compositions may be employed, for example, kidney cell replacement therapy or for testing drug effects on kidneys.

In certain embodiments, provided herein are synthetic tissue scaffold comprising a cell-compatible biopolymer and an isolated population of podocytes distributed therein, wherein the isolated population of podocytes is produced by the methods and compositions described herein. Examples of a cell-compatible biopolymer include, but are not limited to, silk fibroin, polyethylene oxide (PEO), polyethylene glycol (PEG), fibronectin, keratin, polyaspartic acid, polylysine, chitin, hyaluronic acid, pectin, polycaprolactone, polylactic acid, polyglycolic acid, polyhydroxyalkanoates, dextrans, polyanhydrides, polymer, PLA-PGA, polyanhydride, polyorthoester, polycaprolactone, polyfumarate, collagen, chitosan, alginate, hyaluronic acid, and/or other biocompatible polymers. Also provided herein is a biological ink comprising the isolated population of podocytes described herein mixed with a viscous extracellular matrix for use in a 3-D printer. In some embodiments, the isolated population of podocytes described herein can be mixed with a viscous gelatin to form a biological ink of podocytes. The resulting biological ink can be fed into a 3-D printer, which is programmed to arrange different cell types, along with other materials, into a precise three-dimensional shape.

In certain embodiments, the podocytes generated by the methods and compositions here are used in different applications where podocytes are required, including, as an in vitro model for a kidney/glomerular disorder, therapeutic applications (e.g., tissue regeneration and/or repair or transplantation), drug discovery and/or developments, and/or tissue engineering. In certain embodiments, the methods comprises culturing in a cell or tissue culture device the isolated population of podocytes described herein.

In some embodiments where normal, healthy podocytes are used, the podocytes can be contacted with an agent that induces the podocytes to acquire at least one phenotypic characteristic associated with a kidney and/or glomerular disorder, thereby modeling a kidney and/or glomerular disorder in vitro. In some embodiments, doxorubicin and/or Adriamycin can be introduced to induce podocytes injury to model a kidney or glomerulus-specific condition in vitro.

In certain embodiments, a method of screening for an agent to reduce at least one phenotypic characteristic of podocytes associated with a kidney and/or glomerular disorder is provided herein. The method comprises (a) culturing the isolated population of podocytes described herein that display at least one phenotypic characteristic associated with the kidney and/or glomerular disorder; (b) contacting the podocytes with a library of candidate agents; and (c) detecting response of the podocytes to the candidate agents to identify an agent based on detection of the presence of a reduction in the phenotypic characteristic of the podocytes associated with the kidney and/or glomerular disorder. The candidate agents can be selected from the group consisting of, for example, proteins, peptides, nucleic acids (e.g., but not limited to, siRNA, anti-miRs, antisense oligonucleotides, and ribozymes), small molecules, and a combination of two or more thereof. The effects of the candidate agents on the podocytes can be determined by measuring response of the cells and comparing the measured response with podocytes that are not contacted with the candidate agents.

In some embodiments, the podocytes generated by the differentiation methods described herein and/or synthetic tissue scaffolds described herein can be used for kidney regeneration or as cell-based therapeutics for treatment of a kidney and/or glomerular disorder (including, e.g., podocyte injury, proteinuria, glomerulosclerosis, diabetic nephropathy, chemotherapy-related nephrotoxicity or combinations thereof). Thus, methods of treating a kidney and/or glomerular disorder are also provided herein. In one embodiment, the method comprises transplanting to a subject in need thereof (e.g., suffering from a kidney and/or glomerular disorder) an isolated population of podocytes generated by the methods herein and/or a synthetic tissue scaffold described herein. In some embodiments, the podocytes and/or the synthetic tissue scaffold can be transplanted at or in close proximity to a pre-determined location of a kidney of the subject. For example, the podocytes and/or the synthetic tissue scaffold can be transplanted at or in close proximity to a damaged area of a kidney of the subject. The transplanted podocytes can migrate and localize into at least one or more glomerular capillary structure of the kidney tissue, thereby facilitate regeneration and/or repair of the kidney tissue. In some embodiments, the podocytes can be encapsulated within permeable matrices prior to implantation. Encapsulation provides a barrier to the host's immune system and inhibits graft rejection and inflammation. Several methods of cell encapsulation can be employed. In some instances, podocytes can be individually encapsulated. In other instances, many cells can be encapsulated within the same matrix.

EXAMPLES

Example 1

Robust and Rapid Induction Conditions for Dorsal Pancreatic Endoderm from Pluripotency This Example describes generating human podocyte cells from induced pluripotent stem cells.

Materials and Methods

1) Split induced pluripotent stem cells (iPSCs) with Accutase at 60-70% confluency and transfer to a Geltrex-coated 35 mm well. Count cells and plate 18,000 cells per $cm^2$ to the basal media. Add 10 µM rock inhibitor and place the well back at 37° overnight.
2) Next day, remove media with rock inhibitor and replace basal media without rock inhibitor. Cells are ready to differentiate the following day.
3) Day 1—Remove the basal media from the cells and add 8 µM CHIR in Advanced RPMI/Glutamax to each well.
4) Day 2—No media change. Leave cells alone.
5) Day 3—Remove the media from the cells and add 8 µM CHIR in Advanced RPMI/Glutamax to each well.
6) Day 4—No media change. Leave cells alone.
7) Day 5—Remove the media from the cells and add 10 ng/ml Activin A in Advanced RPMI/Glutamax to each well.
8) Day 6—No media change. Leave cells alone.
9) Day 7—Remove the media from the cells and add 10 ng/ml Activin A in Advanced RPMI/Glutamax to each well.
10) Day 8—Remove the basal media from the cells and add 10 ng/ml Fgf9 in Advanced RPMI/Glutamax to each well.
11) Day 9—No media change. Leave cells alone.
12) Day 10—Change to Podocyte Matrix Media. Cells can either be treated on the plates they are on (In situ Differentiation Option) or transferred to new plate, slide or transwell (Cell Transfer Option).

In situ Differentiation Option:
a) Remove media and change to the media containing the podocyte matrix.

Cell Transfer Option:
  b) Coat surfaces with Laminin 521 following directions from Biolamina for at least 3 hours.
  c) Wash cells twice with PBS.
  d) Put 1 mL of Accutase in 35 mm size well (or 1 well of a 6-well plate) for 5-10 minutes in a 37° incubator.
  e) Gently pipet cells up and down.
  f) Add 4 mL pre-warmed Advanced RPMI/Glutamax and spin for 5 minutes at 1000 rpm.
  g) Remove supernatant and discard.
  h) Resuspend the pellet in 1 mL of Advanced RPMI/Glutamax and count cells.
  i) Transfer cells in the media containing the podocyte matrix in the pre-coated slides. E.g., transfer around 27,000 cells per cm$^2$.
  j) Leave the slides at room temperature for 30 minutes and then put slides back into 37°.
13) Day 11—No media change. Leave cells alone.
14) Day 12—Remove media and replace with fresh podocyte matrix.
15) Day 13—Process cells for downstream application. Alternatively, cells can be pulled out longer (up to 17 days) by alternating days of no treatment with days where the media was replaced with fresh podocyte matrix.

Notes
1) Steps #3-11 are adapted from Morizane et al., 2015
2) Prewarm Advanced RPMI/Glutamax for 5 to 10 minutes before using.
3) If differentiating iPSCs, once can use 10 µM CHIR and 5 ng/ml Noggin, as suggested by Morizane et al., 2015.
4) On Day 10, it is recommend to accutase the cells and placing them on Laminin-521 coated slides/wells. Cells can be left on the original wells, but the transfer of the cells in podocyte matrix media to new plates/slides cleans up cell death due to overcrowding.
5) One can use Advanced RPMI/Glutamax or CDM2 as the basal media for differentiation. One can switch from Advanced RPMI/Glutamax to CDM2 on Day 10.

Media
Podocyte Matrix

| | |
|---|---|
| 25 nM | FGFR inhibitor (BGJ398) |
| 30 ng/mL | BMP4 |
| 30 ng/mL | BMP7 |
| 1 µM | LPA |
| 100 nM | IWP2 |
| 100 nM | XX inhibitor (γ-secretase inhibitor) |
| 125 nM | LDN193189 in either Advanced RPMI/Glutamax or CDM2 (see Note 5) |

CDM2 (Loh et al. (2014) Cell Stem Cell 14(2):237-52)
  50% IMDM
  50% F12
  1 mg/ml Polyvinyl Alcohol
  1% v/v Chemically Defined Lipid Concentrate
  450 uM Monothioglycerol
  0.7 ug/ml Insulin
  15 ug/ml Transferrin
1. Prepare Insulin Stock Solution.
  100 mg insulin crystalline powder is dissolved in 10 ml of double distilled autoclaved water (final concentration of 10 mg/ml)
2. Prepare Media Supplement.
  70 µl of insulin (10 mg/ml)
  500 µl of transferrin
  10 ml of chemically defined lipid concentrate
  39 µl of Monothioglycerol
  Aliquot 1,060.9 µl/tube and store at −20° C. One aliquot of supplements is used to prepare 100 ml of CDM2.
3. Prepare CDM2 (100 ml)
  Thaw one aliquot of the media supplement.
  100 mg PVA is weighed out and placed into a beaker. Add 50 mL of IMDM media and stir until dissolve.
  50 ml of F12 are added to the top of a bottle top filter.
  The previously prepared IMDM/PVA tube is also then added to the top of a bottle top filter.
  The thawed insulin/transferrin/lipid/monothioglycerol aliquot is added to the top of a bottle top filter.
  If penicillin and streptomycin is needed in the medium add 1 ml of a 1/100 solution to the top of a bottle top filter.
  Add 1 mL of L-glutamine.
  Vacuum filter, remove the bottle top filter and label with date.
  CDM2 media is good for about 2 weeks.

TABLE 1

Reagents

| Effectors/Inhibitors | Vendor | Catalog# |
|---|---|---|
| Accutase | StemCell Technologies | 07920 |
| Advanced RPMI | Life Technologies | 12633012 |
| BGJ398 (FGF inhibitor) | Selleckchem | S2183 |
| Chemically Defined Lipid Concentrate | Gibco | 11905-031 |
| CHIR99021 (CHIR) | LC Laboratories | C-6556 |
| Geltrex | ThermoFisher | A1413302 |
| Glutamax | Life Technologies | 35050-061 |
| Insulin | Roche | 1376497 |
| IWP2 | Selleckchem | S7085 |
| Laminin-521 | Biolamina | LN521-02 |
| LDN193189 | StemCell Technologies | 72142 |
| Lysophosphatidic Acid (LPA) | Santa Cruz Biotech | 325465-93-8 |
| Monothioglycerol | Sigma | M6145 |
| Noggin | Peprotech | 120-10C |
| Polyvinyl Alcohol | Sigma | P8136 |
| Recombinant Activin A | Peprotech | 120-14 |
| Recombinant Bmp4 | Peprotech | 120-05ET |
| Recombinant Bmp7 | Peprotech | 120-03 |
| Recombinant Fgf9 | R&D Systems | 273-F9-025 |
| Transferrin | Roche | 652202 |
| XX (g-Secretase inhibitor) | Millipore/Sigma | 565789 |
| Y-27632 (rock inhibitor) | Tocris | 1254 |

Figure 3:
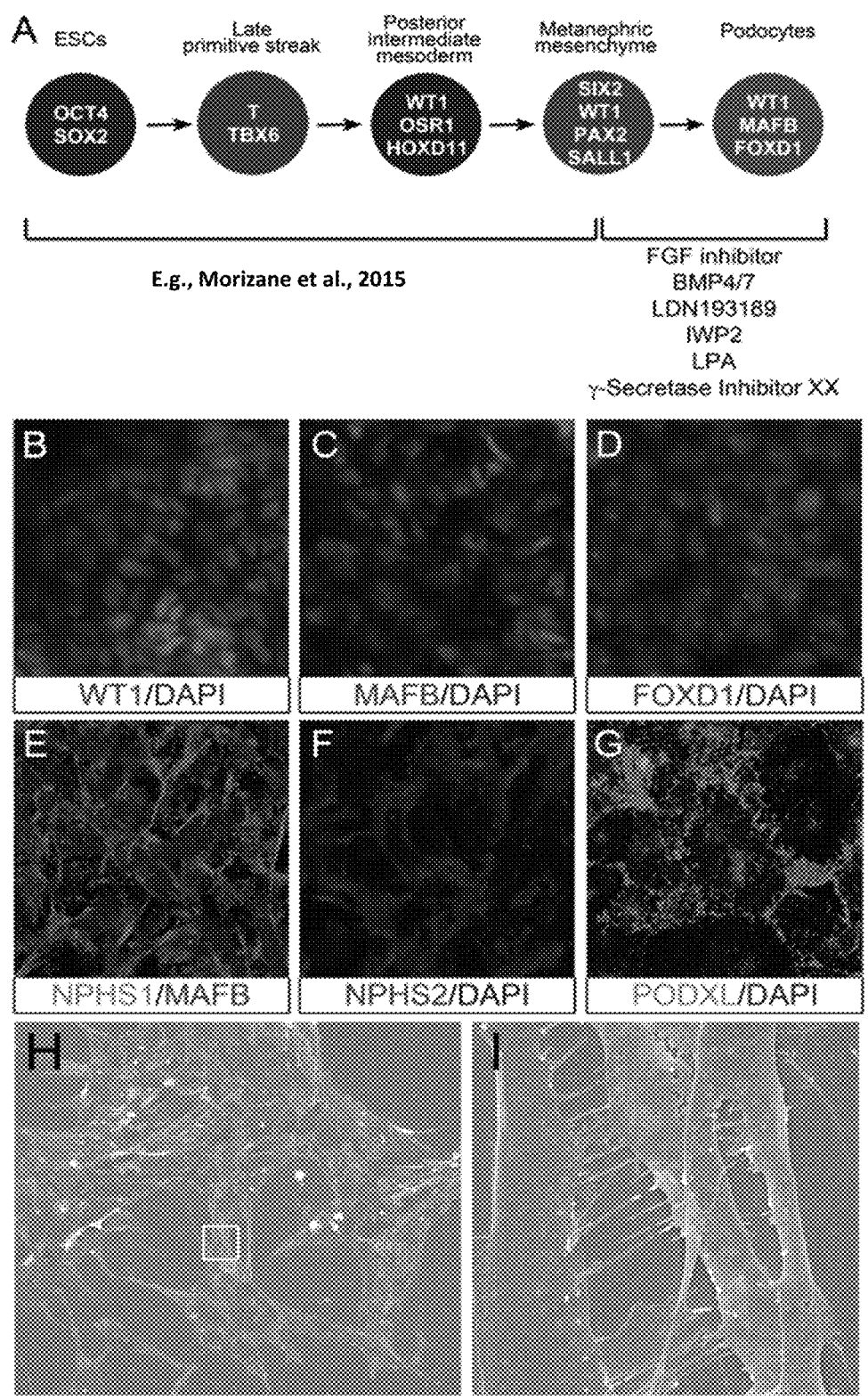
FIG. 3: Differentiation of Human Stem Cells into Podocytes. (A) Schematic of the differentiation scheme used to obtain podocytes from embryonic stem cells. Metanephric mesenchyme formation was achieved following the protocol established by Morziane et al., 2015. 33(11): p. 1193-1200, herein incorporated by reference in its entirety. The factor combination used to promote podocyte differentiation is indicated. (B-G) Immunofluorescence analysis for the expression of the podocyte transcription factors WT1, MAFB and FOXD1 as well as the structural podocyte proteins, NPHS1, NPHS2 and PODXL. Nuclei were counterstained with DAPI (blue). The cells acquire a classical podocyte phenotype with foot processes labeled by NPHS1 and NPHS2 and the apical domain labeled by PODXL. (H,I) Scanning Electron Microscopy (SEM) shows the formation of foot processes between isolated podocytes. (I) is a close up of the area indicated by the white box in (H).
Figure 4:
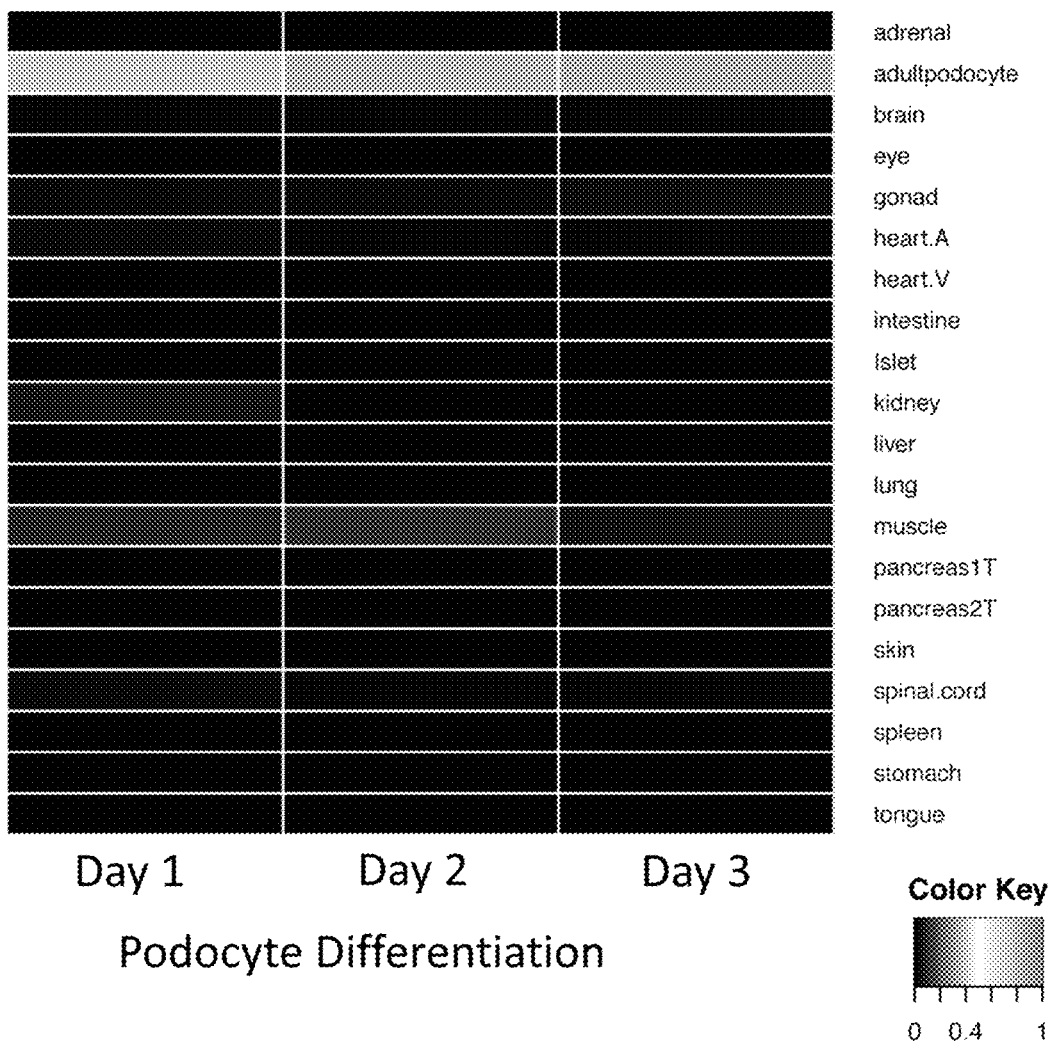
FIG. 4: KeyGene Analysis of Podocyte Differentiation. Stem cell-derived podocytes were processed for transcriptome analysis 1, 2 and 3 days post podocyte induction. Data were processed for KeyGen analysis comparing it to the transcriptomes of multiple human organs. Green shading indicates the significant transcriptional match between adult podocytes and the stem cell-derived podocytes.
Figure 5:
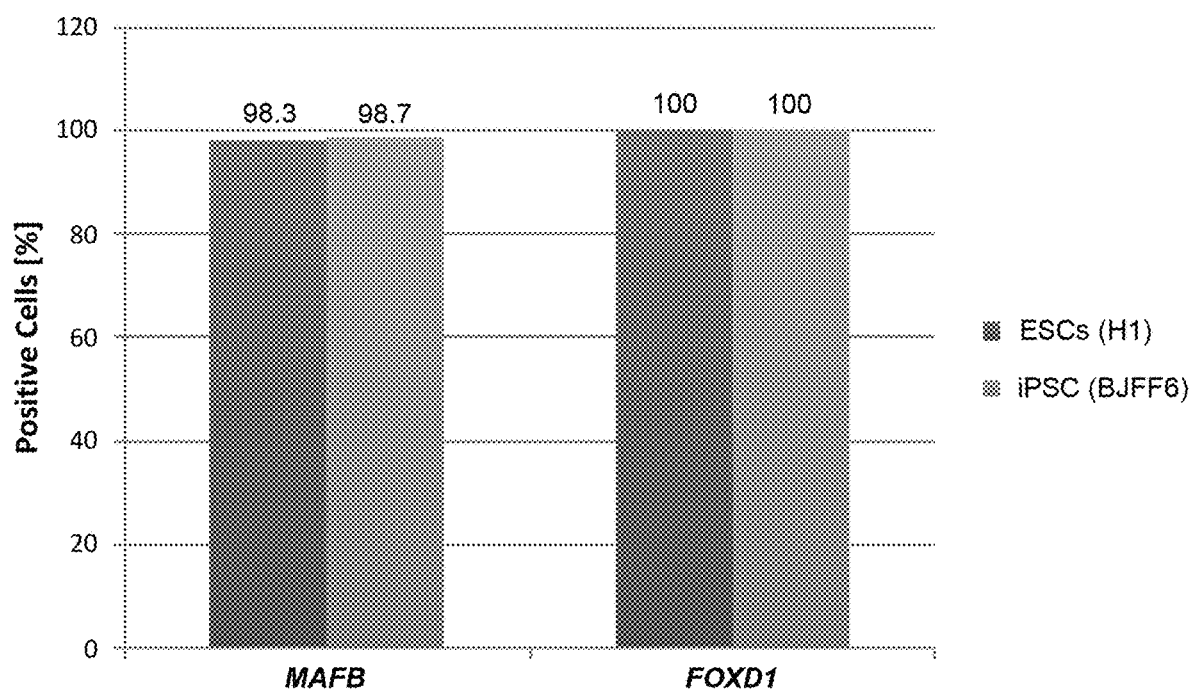
FIG. 5: Efficacy of Podocyte Differentiation. Embryonic stem cells (ESCs, clone H1) or iPSCs (clone BJFF6) were differentiated into podocytes using a stepwise differentiation protocol. Cells were analyzed by immunofluorescence for the expression of the podocyte-specific transcription factors MAFB and FOXD1. Graph presents the percentage of nuclei expressing either transcription factor and is also indicated by the numbers on top of the bars. Note the near complete conversion of the culture in MAFB/FOXD1-positive cells.
Figure 6:
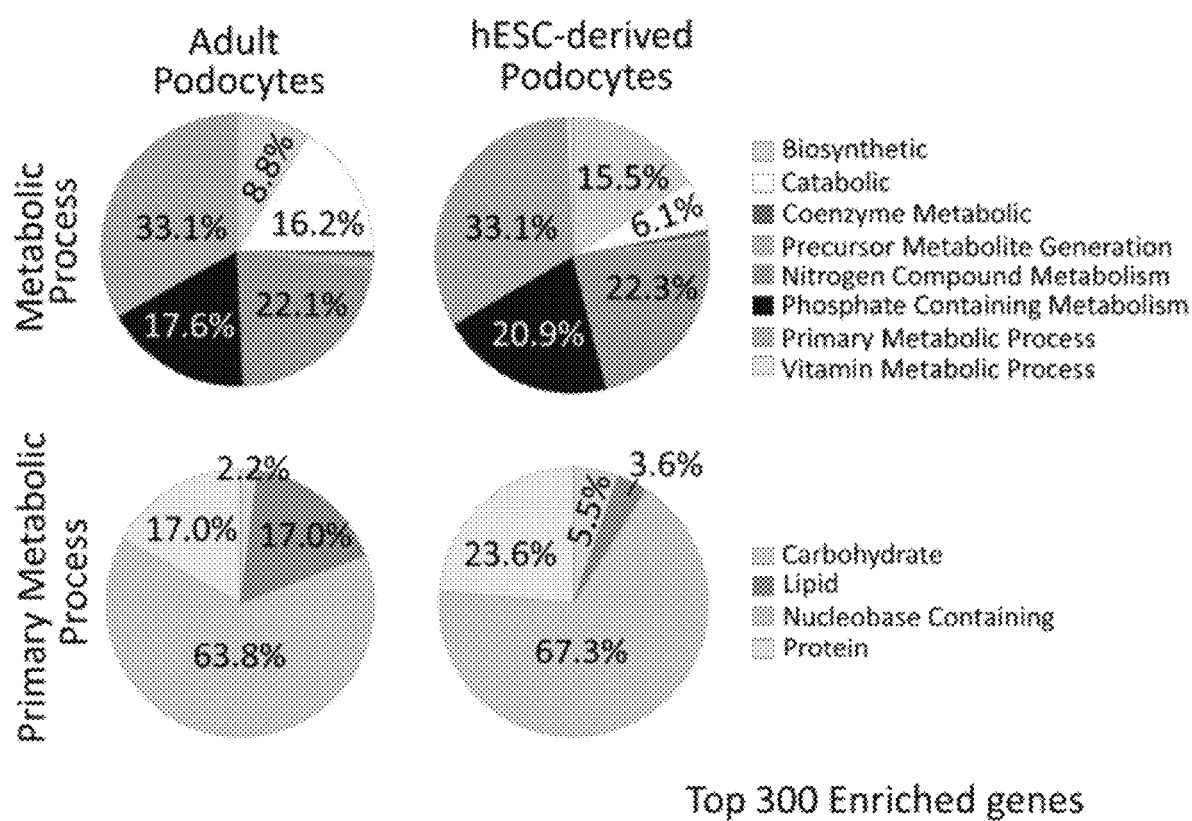
FIG. 6. Metabolic Characterization of Stem Cell-Derived Podocytes. Transcriptome analysis comparing metabolic processes in adult podocytes (right pie diagrams) and stem cell-derived podocytes (right pie diagrams) demonstrate a close similarity of the two cell populations. The upper panels show the distribution of all metabolic processes, while the bottom panels show a breakdown of the primary metabolic processes (orange pie in the top panels).

Results
Following the protocol above using the podocyte matrix agents resulted in the direct induction of podocytes from nephron progenitor cells (FIG. 3A). The podocytes are characterized by a robust induction of podocyte genes by qRT-PCR (e.g. WT1, MAFB, FOXC2, TCF21, FOXD1 and the structural proteins NPHS1, NPHS2 and PODXL). The establishment of stem cell-derived podocytes is corroborated by immunofluorescence, cell morphology and ultrastructural studies (FIG. 3B-I). The efficacy of the podocyte differentiation can be confirmed by transcriptome analysis demonstrating that the stem cell-derived podocytes most closely resemble adult podocytes found in the adult human kidney (FIG. 4). Importantly, the protocol does not require the addition of serum, is robust and can induce podocytes from multiple stem cell lines (Embryonic Stem Cells (ESCs) and induced pluripotent stem cells (iPSCs)) at a similar efficiency (>90% cell conversion) (FIG. 5).

REFERENCES

1. Marinho et al., Sci Rep, 2015. 5: p. 9834.
2. Morizane, et al., 2015. 33(11): p. 1193-1200.

3. Chinese patent CN105087467.
4. European patent EP3027737.
5. Rauch et al., PLoS ONE 13(9): e0203869.
6. Krtil et al., Kidney Blood Press Res. 2007; 30(3):162-74.
7. Musah et al., Nat Biomed Eng. 2017; 1. pii: 0069.
8. Song et al., PLoS One. 2012; 7(9):e46453.
9. Ronconi et al., J Am Soc Nephrol. 2009 February; 20(2):322-32.

All publications and patents mentioned in the specification and/or listed below are herein incorporated by reference. Various modifications and variations of the described method and system of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the relevant fields are intended to be within the scope described herein.

We claim:

1. A method of generating podocyte cells comprising:
   a) contacting a population of nephron progenitor cells with an FGFR pathway inhibitor, a BMP pathway inhibitor, a γ secretase inhibitor BMP4, BMP7, and a WNT pathway inhibitor; and
   b) culturing at least a portion of said population of nephron progenitor cells such that a population of podocyte cells is generated.
2. The method of claim 1, wherein said podocytes express the following genes: WT1, MAFB, and FOXC2.
3. The method of claim 1, wherein said nephron progenitor cells are not exposed to serum during said culturing or during said contacting.
4. The method of claim 1, wherein said FGFR pathway inhibitor comprises BGJ398.
5. The method of claim 1, wherein said BMP pathway inhibitor comprise LDN193189.
6. The method of claim 1, wherein said WNT pathway inhibitor comprises IWP2.
7. The method of claim 1, further comprising, prior to step b), contacting said nephron progenitor cells with lysophosphatidic acid (LPA).
8. The method of claim 1, wherein said γ secretase inhibitor is gamma-secretase inhibitor XX.
9. The method of claim 1, wherein said BMP pathway inhibitor is selected from the group consisting of: DMIH1, DMH2, Dorsopmorphin, K02288, LDN214117, ML347, and Noggin.
10. The method of claim 1, wherein said FGFR pathway inhibitor is selected from the group consisting of: PD0325901, Arctigenin, PD184352, PD198306, PD334581, SL 327, U0126, a MEK inhibitor, a FGFR inhibitor, a MAPK inhibitor, MEK162, GSK1120212, PD325901, CI-1040, TAK-733, Selumetinib and XL518.
11. The method of claim 1, wherein said culturing is conducted for 1-5 days or 2-4 days.
12. The method of claim 1, wherein said nephron progenitor cells are not exposed to a transforming growth factor beta (TGFβ) pathway agonist during said culturing or during said contacting.

* * * * *